US011054430B2

(12) United States Patent
von Borstel et al.

(10) Patent No.: US 11,054,430 B2
(45) Date of Patent: Jul. 6, 2021

(54) COMPOUNDS AND METHODS FOR THE DETECTION OF METHOTREXATE

(71) Applicant: Defined Diagnostics, LLC, Rockville, MD (US)

(72) Inventors: Reid von Borstel, Potomac, MD (US); Paul Hu, Frederick, MD (US); Xiaofen Huang, Gaithersburg, MD (US); Jeffrey Allan Miller, Lincoln University, PA (US)

(73) Assignee: Defined Diagnostics, LLC, Rockville, MD (US)

( * ) Notice: Subject to any disclaimer, the term of this patent is extended or adjusted under 35 U.S.C. 154(b) by 0 days.

(21) Appl. No.: 15/746,404

(22) PCT Filed: Jul. 7, 2016

(86) PCT No.: PCT/US2016/041266
§ 371 (c)(1),
(2) Date: Jan. 19, 2018

(87) PCT Pub. No.: WO2017/007889
PCT Pub. Date: Jan. 12, 2017

(65) Prior Publication Data
US 2018/0328952 A1    Nov. 15, 2018

Related U.S. Application Data

(60) Provisional application No. 62/189,831, filed on Jul. 8, 2015.

(51) Int. Cl.
*G01N 33/94* (2006.01)
*C07K 16/44* (2006.01)

(52) U.S. Cl.
CPC ......... *G01N 33/9493* (2013.01); *C07K 16/44* (2013.01); *C07K 2317/33* (2013.01); *C07K 2317/56* (2013.01)

(58) Field of Classification Search
CPC . G01N 33/9493; C07K 16/44; C07K 2317/56
See application file for complete search history.

(56) References Cited

U.S. PATENT DOCUMENTS

| | | | |
|---|---|---|---|
| 4,751,190 A | 6/1988 | Chiapetta et al. | |
| 5,382,582 A | 1/1995 | Chan | |
| 5,578,289 A | 11/1996 | Pomato et al. | |
| 5,698,556 A | 12/1997 | Chan | |
| 5,962,218 A * | 10/1999 | Leland | C12Q 1/6825 435/6.11 |
| 6,063,581 A | 5/2000 | Sundrehagen | |

FOREIGN PATENT DOCUMENTS

| | | |
|---|---|---|
| EP | 0079489 A1 | 5/1983 |
| WO | 1995/016026 A1 | 6/1995 |

OTHER PUBLICATIONS

Myers et al. (Proc. Nat. Acad. Sci. 1975 Vol. 72, p. 3683-3686). (Year: 1975).*
The International Search Report for International Application No. PCT/US2016/041266, dated Dec. 8, 2016.
The Written Opinion for International Application No. PCT/US2016/041266, dated Dec. 8, 2016.
ARK Diagnostics, Inc. ARK Methotrexate Assay. Aug. 2011, Downloaded from http://www.ark-tdm.com/pdfs/MethotrexateAssay_Rev02.pdf.
Suh-Lailam et al., Performance Characteristics of Three Assays for the Therapeutic Drug Monitoring of Methotrexate. 2013, Downloaded from https://www.aruplab.com/Research&Development/resources/Posters/2013/Johnson%20Davis_IATDMCT_2013.pdf.
Widemann, et al., "Dihydrofolate Reductase Enzyme Inhibition Assay for Plasma Methotrexate Determination Using a 96-Well Microplate Reader.", Clinical Chemistry, vol. 45, No. 2, Feb. 1999 (Feb. 1, 1999), pp. 223-228, XP055346193.
Adamson, et al., "Methotrexate Pharmacokinetics Following Administration of Recombinant Carboxypeptidase-G2 in Rhesus Monkeys.", Journal of Clinical Oncology, vol. 10, No. 8, Aug. 1992 (Aug. 1, 1992), pp. 1359-1364, XP055346195.
Smalley, et al., "An immunoassay for measurement of methotrexate on ARCHITECT i system", Cancer Research, vol. 74, No. 19, Oct. 2014 (Oct. 1, 2014), pp. 3678, XP055346189.

* cited by examiner

*Primary Examiner* — Changhwa J Cheu
(74) *Attorney, Agent, or Firm* — Lewis J. Kreisler

(57) ABSTRACT

The disclosure relates generally to methods of detecting and quantifying methotrexate (MTX) in a sample. The methods disclosed herein decrease cross-reactivity and improve sensitivity of the detection.

12 Claims, 5 Drawing Sheets

Specification includes a Sequence Listing.

SEQUENCE LISTING

```
<160> NUMBER OF SEQ ID NOS: 12

<210> SEQ ID NO 1
<211> LENGTH: 354
<212> TYPE: DNA
<213> ORGANISM: mouse

<400> SEQUENCE: 1
gaggtgcagc tggtggagtc tgggggaggc ttagtgaagc ctggagggtc cctgagactc      60
tcctgtgcag cctctggatt cactttcagg acttatgcca tgtcttgggt tcgccagact     120
ccggagaaga gactggaatg ggtcgcgacc attactagtg gtggtactta tatttattat     180
ttagacagtg tgaagggtcg attcaccatc tccagagaca atgccaagaa tgttctgtac     240
ctgcaaatga gcagtctgag gtctgaggac acggccatgt attactgtgt aagactctat     300
ggttacgacg gtatggacta ctggggtcaa ggaacctcag tcaccgtctc cgca           354

<210> SEQ ID NO 2
<211> LENGTH: 328
<212> TYPE: DNA
<213> ORGANISM: mouse

<400> SEQUENCE: 2
caggctgttg tgactcagga atctgcactc accacatcac caggtgaaac agtcacactc      60
acttgtcgct caagtactgg ggctgtttca actagtaatt atgtcaactg ggtccaagag     120
aaaccagatc atttattcac tggtctaata ggtggtacca aaaaccgagt tccaggtgtt     180
cctgccagat tctcaggctc cctgattgga gacaaggctg ccctcaccat cacaggggca     240
cagactgagg atgaggcaat atatttctgt gctctatggt acaccaacca tttggtgttc     300
ggtggaggaa ccaaactgac tgtcctag                                        328

<210> SEQ ID NO 3
<211> LENGTH: 118
<212> TYPE: PRT
<213> ORGANISM: mouse

<400> SEQUENCE: 3
```

```
Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Arg Thr Tyr
            20                  25                  30

Ala Met Ser Trp Val Arg Gln Thr Pro Glu Lys Arg Leu Glu Trp Val
        35                  40                  45

Ala Thr Ile Thr Ser Gly Gly Thr Tyr Ile Tyr Tyr Leu Asp Ser Val
    50                  55                  60

Lys Gly Arg Phe Thr Ile Ser Arg Asp Asn Ala Lys Asn Val Leu Tyr
65                  70                  75                  80

Leu Gln Met Ser Ser Leu Arg Ser Glu Asp Thr Ala Met Tyr Tyr Cys
                85                  90                  95

Val Arg Leu Tyr Gly Tyr Asp Gly Met Asp Tyr Trp Gly Gln Gly Thr
            100                 105                 110

Ser Val Thr Val Ser Ala
        115
```

<210> SEQ ID NO 4
<211> LENGTH: 109
<212> TYPE: PRT
<213> ORGANISM: mouse

<400> SEQUENCE: 4

```
Gln Ala Val Val Thr Gln Glu Ser Ala Leu Thr Thr Ser Pro Gly Glu
1               5                   10                  15

Thr Val Thr Leu Thr Cys Arg Ser Ser Thr Gly Ala Val Ser Thr Ser
            20                  25                  30

Asn Tyr Val Asn Trp Val Gln Glu Lys Pro Asp His Leu Phe Thr Gly
        35                  40                  45

Leu Ile Gly Gly Thr Lys Asn Arg Val Pro Gly Val Pro Ala Arg Phe
    50                  55                  60

Ser Gly Ser Leu Ile Gly Asp Lys Ala Ala Leu Thr Ile Thr Gly Ala
65                  70                  75                  80

Gln Thr Glu Asp Glu Ala Ile Tyr Phe Cys Ala Leu Trp Tyr Thr Asn
                85                  90                  95

His Leu Val Phe Gly Gly Gly Thr Lys Leu Thr Val Leu
            100                 105
```

<210> SEQ ID NO 5
<211> LENGTH: 354
<212> TYPE: DNA
<213> ORGANISM: mouse

<400> SEQUENCE: 5

```
cagatccagt tggtgcagtc tggacctgag ctgaagaggc ctggagagac ggtcaagatc      60
tcctgcaagg cttctggata tacctataca tattatggaa ttaactggtt gaaacaggcg     120
ccaggaaagg atttaaagtg gatgggctgg ataaacccct acactggaga gccagcatat     180
gctgatgact caagggacg gtttgccttc tctttggaaa cctctgccac tactacctat     240
ttgcagatca caaccctcaa aaatgaggac atggctacat atttctgtgc aagaaatagc     300
tattattatg ctctggacta ctggggtcaa ggaacctcag tcaccgtctc ctca           354
```

<210> SEQ ID NO 6
<211> LENGTH: 337
<212> TYPE: DNA
<213> ORGANISM: mouse

<400> SEQUENCE: 6

```
gatgttgtga tgacccaaac tcccctctcc ctgcctgtca atcttggaga tcaagcctcc    60
atctcttgca gatctagtca gaatcttgta aaaagtaatg gaaacaccta cttacattgg   120
ttcctgcaga agccaggcca gtctccaaag ctcctgatct acaaagtttc caatcgattt   180
tctggggtcc cagacaggtt cagtggcagt ggatcaggga cagatttcac actcaagatc   240
agcagagtgg aggctgagga tctgggagtt tatttctgtt ctcaaagtac acatgttccg   300
tggacgttcg gtggaggcac caagctggaa atcaaac                            337
```

<210> SEQ ID NO 7
<211> LENGTH: 118
<212> TYPE: PRT
<213> ORGANISM: mouse

<400> SEQUENCE: 7

```
Gln Ile Gln Leu Val Gln Ser Gly Pro Glu Leu Lys Arg Pro Gly Glu
 1               5                  10                  15
Thr Val Lys Ile Ser Cys Lys Ala Ser Gly Tyr Thr Tyr Thr Tyr Tyr
            20                  25                  30
Gly Ile Asn Trp Leu Lys Gln Ala Pro Gly Lys Asp Leu Lys Trp Met
        35                  40                  45
Gly Trp Ile Asn Pro Tyr Thr Gly Glu Pro Ala Tyr Ala Asp Asp Phe
    50                  55                  60
Lys Gly Arg Phe Ala Phe Ser Leu Glu Thr Ser Ala Thr Thr Thr Tyr
65                  70                  75                  80
Leu Gln Ile Asn Asn Leu Lys Asn Glu Asp Met Ala Thr Tyr Phe Cys
                85                  90                  95
Ala Arg Asn Ser Tyr Tyr Tyr Ala Leu Asp Tyr Trp Gly Gln Gly Thr
            100                 105                 110
Ser Val Thr Val Ser Ser
        115
```

<210> SEQ ID NO 8
<211> LENGTH: 112
<212> TYPE: PRT
<213> ORGANISM: mouse

<400> SEQUENCE: 8

```
Asp Val Val Met Thr Gln Thr Pro Leu Ser Leu Pro Val Asn Leu Gly
 1               5                  10                  15
Asp Gln Ala Ser Ile Ser Cys Arg Ser Ser Gln Asn Leu Val Lys Ser
            20                  25                  30
Asn Gly Asn Thr Tyr Leu His Trp Phe Leu Gln Lys Pro Gly Gln Ser
        35                  40                  45
Pro Lys Leu Leu Ile Tyr Lys Val Ser Asn Arg Phe Ser Gly Val Pro
    50                  55                  60
Asp Arg Phe Ser Gly Ser Gly Ser Gly Thr Asp Phe Thr Leu Lys Ile
65                  70                  75                  80
Ser Arg Val Glu Ala Glu Asp Leu Gly Val Tyr Phe Cys Ser Gln Ser
                85                  90                  95
Thr His Val Pro Trp Thr Phe Gly Gly Gly Thr Lys Leu Glu Ile Lys
            100                 105                 110
```

<210> SEQ ID NO 9
<211> LENGTH: 354
<212> TYPE: DNA

<210> SEQ ID NO 9
<211> LENGTH: 354
<212> TYPE: DNA
<213> ORGANISM: mouse

<400> SEQUENCE: 9
cagatccagt tggtgcagtc tggacctgag ctgaagaagc tggagagaca agtcaagatc      60
tcctgcaagg cttctgggta taccttcaca aactatggaa tgaactgggt gaagcgggct     120
ccaggaaagg gtttaaagtg gatgggctgg atcaatccct acactggaga gccaacatat     180
gctgatgact tcaagggacg gtttgccttc tctttggaaa cctctgccag cactgcctat     240
ttgcagatca acaacctcaa aaatgaggac atggctacat atttctgtgc aagaaacgac     300
tattactatg ctttggactc ctggggtcaa ggaacctcag tcaccgtctc ctca           354

<210> SEQ ID NO 10
<211> LENGTH: 337
<212> TYPE: DNA
<213> ORGANISM: mouse

<400> SEQUENCE: 10
gatgttgtga tgacccaaag tccactctcc ctgcctgtca gtcttggaga tcaagcctcc      60
atctcttgca gatctagtca gagccttgta aaaagtaatg aaataccta tttgcattgg     120
ttcctgcaga agtcaggcca gtctccaaag ctcctgatct acaaagtttc caaccgattt     180
tctggggtcc cagacaggtt cagtggcagt ggatcaggga cagatttcac actcaagatc     240
agcagagtgg aggctgagga tctgggagtt tatttctgct ctcaaagtac acatgttccg     300
tggacgttcg gtggaggcac caagctggaa atcaaac                              337

<210> SEQ ID NO 11
<211> LENGTH: 118
<212> TYPE: PRT
<213> ORGANISM: mouse

<400> SEQUENCE: 11

Gln Ile Gln Leu Val Gln Ser Gly Pro Glu Leu Lys Lys Pro Gly Glu
1               5                   10                  15

Thr Val Lys Ile Ser Cys Lys Ala Ser Gly Tyr Thr Phe Thr Asn Tyr
            20                  25                  30

Gly Met Asn Trp Val Lys Arg Ala Pro Gly Lys Gly Leu Lys Trp Met
        35                  40                  45

Gly Trp Ile Asn Pro Tyr Thr Gly Glu Pro Thr Tyr Ala Asp Asp Phe
    50                  55                  60

Lys Gly Arg Phe Ala Phe Ser Leu Glu Thr Ser Ala Ser Thr Ala Tyr
65                  70                  75                  80

Leu Gln Ile Asn Asn Leu Lys Asn Glu Asp Met Ala Thr Tyr Phe Cys
                85                  90                  95

Ala Arg Asn Asp Tyr Tyr Tyr Ala Leu Asp Ser Trp Gly Gln Gly Thr
            100                 105                 110

Ser Val Thr Val Ser Ser
        115

<210> SEQ ID NO 12
<211> LENGTH: 112
<212> TYPE: PRT
<213> ORGANISM: mouse

<400> SEQUENCE: 12

Asp Val Val Met Thr Gln Ser Pro Leu Ser Leu Pro Val Ser Leu Gly
1               5                   10                  15

```
Asp Gln Ala Ser Ile Ser Cys Arg Ser Ser Gln Ser Leu Val Lys Ser
            20                  25                  30

Asn Gly Asn Thr Tyr Leu His Trp Phe Leu Gln Lys Ser Gly Gln Ser
        35              40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70              75                      80

Ser Arg Val Glu Ala Glu Asp Leu Gly Val Tyr Phe Cys Ser Gln Ser
                85              90                  95

Thr His Val Pro Trp Thr Phe Gly Gly Gly Thr Lys Leu Glu Ile Lys
                100             105             110
```

COMPOUNDS AND METHODS FOR THE DETECTION OF METHOTREXATE

This is a national stage application of International Application No. PCT/US2016/041266, filed internationally on Jul. 7, 2016, which claims priority to U.S. Provisional Patent Application No. 62/189,831, filed Jul. 8, 2015, each of which is herein incorporated by reference in its entirety.

FIELD

The present disclosure relates to the field of assays for determining the presence of and/or quantifying the amount of methotrexate (MTX) in biological samples.

BACKGROUND

Methotrexate (MTX) is a clinically important antifolate drug, which competitively inhibits dihydrofolate reductase (DHFR), thereby impairing folate production. Folate is necessary for the de novo synthesis of thymidine, required for DNA synthesis. Folate is also required for purine base synthesis of DNA, RNA, thymidylates, and proteins. Thus, methotrexate impairs synthesis of thymidine and other metabolites crucial for cell proliferation.

High-dose methotrexate protocols can be curative in some cancers including osteosarcoma and acute lymphoid leukemia (ALL), but carry a risk of severe or life-threatening toxicity. In such protocols, a high dose of methotrexate is administered by infusion, and then leucovorin (folinic acid) is administered to prevent or lessen the side-effects of methotrexate. The dose and timing of leucovorin rescue is critical, since too much leucovorin can reduce anticancer efficacy of methotrexate, and too little can lead to unnecessary toxicities.

An additional issue in high dose methotrexate protocols is that methotrexate and its metabolites can precipitate in the kidneys, thereby impairing methotrexate elimination, leading to the potential for extremely serious toxicity. An exogenous antidotal carboxypeptide enzyme, glucarpidase (Voraxaze® by BTG International, Inc.), converts methotrexate to its inactive metabolites DAMPA (4-amino-4-deoxy-N-10-methylpteroic acid) and glutamate. DAMPA and glutamate can then be metabolized by the liver, providing an alternative route of methotrexate elimination by renal clearance during high-dose methotrexate treatment.

Measurement of plasma methotrexate is a routine component of high-dose methotrexate protocols, because the success of the regimens depends on methotrexate concentration-guided selection of leucovorin doses and detection of methotrexate clearance problems due to renal impairment (whether due to precipitation of methotrexate and metabolites, or to renal impairment from other causes). Furthermore, patients are generally not discharged from hospital care until plasma methotrexate is below a level associated with unacceptable toxicity.

Many factors, including dosages, individual metabolism rate and other clinical factors, can affect MTX plasma concentrations. In some treatments, MTX plasma levels can reach as high as 3.1 mMol/L after an initial 4-hour i.v. infusion. MTX concentrations typically decrease to levels between 30-300 µMol/L at 24 hours, between 3.0-30 µMol/L at 48 hours and <0.3 µMol/L at 72 hours. MTX dosages may be adjusted if plasma levels fall below target concentrations. If MTX levels exceed target plasma levels, leucovorin rescue therapy may be administered. After MTX treatment, many clinical centers may decide to discharge patients when plasma MTX concentrations fall below 0.05 or 0.10 µMol/L.

Methotrexate monitoring is generally performed via clinical laboratory assays which can have certain drawbacks. For example, MTX can be accurately detected with HPLC-MS. However, the detection needs considerable lab setup, extensive sample preparation procedures and often requires long turn-around time, and may display lab-to-lab variability. There are also several existing commercial MTX immunoassays. However, these immunoassays have high cross-reactivity with DAMPA, which is a metabolite of MTX when glucarpidase is used and remains in circulation for 5-6 days. As a result, these assays may not be suitable for measuring MTX plasma concentrations for patients on high dose MTX therapy.

There exists a need for a highly sensitive quantitative methotrexate assay with low cross-reactivity with DAMPA and 7-hydroxymethotrexate (7-OH-MTX).

SUMMARY

The present disclosure relates generally to antibodies having binding specificity to methotrexate.

The present disclosure relates generally to antibodies having binding specificity to methotrexate and a variable heavy chain and a variable light chain, wherein the variable heavy chain nucleotide sequence comprises SEQ ID NO:1 and wherein the variable light chain nucleotide sequence comprises SEQ ID NO:2.

The present disclosure relates generally to antibodies having binding specificity to methotrexate and a variable heavy chain and a variable light chain, wherein the variable heavy chain nucleotide sequence comprises SEQ ID NO:5 and wherein the variable light chain nucleotide sequence comprises SEQ ID NO:6.

The present disclosure relates generally to antibodies having binding specificity to methotrexate and a variable heavy chain and a variable light chain, wherein the variable heavy chain nucleotide sequence comprises SEQ ID NO:9 and wherein the variable light chain nucleotide sequence comprises SEQ ID NO:10.

The present disclosure relates generally to antibodies having binding specificity to methotrexate and a variable heavy chain and a variable light chain, wherein the variable heavy chain amino acid sequence comprises SEQ ID NO:3 and wherein the variable light chain amino acid sequence comprises SEQ ID NO:4.

The present disclosure relates generally to antibodies having binding specificity to methotrexate and a variable heavy chain and a variable light chain, wherein the variable heavy chain amino acid sequence comprises SEQ ID NO:7 and wherein the variable light chain amino acid sequence comprises SEQ ID NO:8.

The present disclosure relates generally to antibodies having binding specificity to methotrexate and a variable heavy chain and a variable light chain, wherein the variable heavy chain amino acid sequence comprises SEQ ID NO:11 and wherein the variable light chain amino acid sequence comprises SEQ ID NO:12.

The present disclosure relates generally to methods of detecting methotrexate (MTX) in a sample, comprising the steps of combining in a solution the sample with a capture molecule and a labeled MTX, wherein the capture molecule is capable of binding the labeled MTX, and wherein MTX when present in the sample competes with the labeled MTX for binding to the capture molecule; and detecting an amount of labeled MTX bound to the capture molecule through signal produced by a label on the bound labeled MTX, wherein the signal is inversely proportional to the amount of MTX present in the sample.

The present disclosure generally relates to kits for detection of methotrexate (MTX) in a sample, the kit comprising a capture molecule; a labeled MTX, wherein the capture molecule is capable of binding the labeled MTX and wherein MTX competitively inhibits binding of the labeled MTX to the capture molecule; and instructions for performing the detection assay, including combining in a solution the sample with a capture molecule and a labeled MTX, wherein the capture molecule is capable of binding the labeled MTX, and wherein MTX when present in the sample competes with the labeled MTX for binding to the capture molecule; and detecting an amount of labeled MTX bound to the capture molecule through signal produced by a label on the bound labeled MTX, wherein the signal is inversely proportional to the amount of MTX present in the sample.

Apart from the subject matter discussed above, the present disclosure includes a number of other exemplary features such as those explained hereinafter. It is to be understood that both the foregoing description and the following description are exemplary only.

BRIEF DESCRIPTION OF THE SEQUENCES

SEQ ID NO:1 is a nucleotide sequence of the variable heavy chain of an antibody 10C7 of the present disclosure.
SEQ ID NO:2 is a nucleotide sequence of the variable light chain of an antibody 10C7 of the present disclosure.
SEQ ID NO:3 is an amino acid sequence of the variable heavy chain of an antibody 10C7 of the present disclosure.
SEQ ID NO:4 is an amino acid sequence of the variable light chain of an antibody 10C7 of the present disclosure.
SEQ ID NO:5 is a nucleotide sequence of the variable heavy chain of an antibody 19A6 of the present disclosure.
SEQ ID NO:6 is a nucleotide sequence of the variable light chain of an antibody 19A6 of the present disclosure.
SEQ ID NO:7 is an amino acid sequence of the variable heavy chain of an antibody 19A6 of the present disclosure.
SEQ ID NO:8 is an amino acid sequence of the variable light chain of an antibody 19A6 of the present disclosure.
SEQ ID NO:9 is a nucleotide sequence of the variable heavy chain of an antibody 6D4 of the present disclosure.
SEQ ID NO:10 is a nucleotide sequence of the variable light chain of an antibody 6D4 of the present disclosure.
SEQ ID NO:11 is an amino acid sequence of the variable heavy chain of an antibody 6D4 of the present disclosure.
SEQ ID NO:12 is an amino acid sequence of the variable light chain of an antibody 6D4 of the present disclosure.

DETAILED DESCRIPTION

Figure 1:
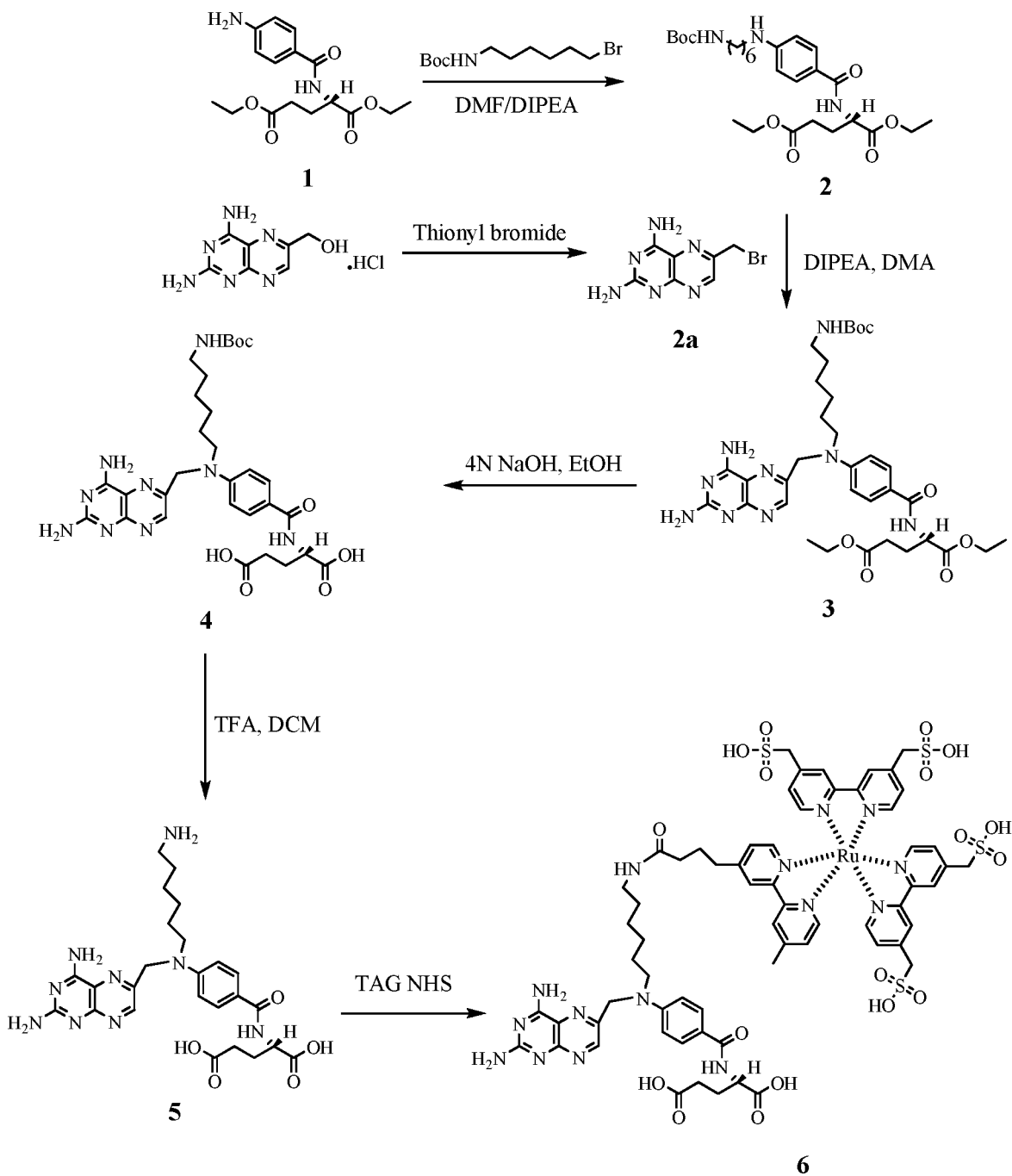
FIG. 1 is a schematic of a chemical synthesis of a compound of the present disclosure.

The disclosure relates generally to methods of detecting and quantifying methotrexate (MTX) in a sample. The methods disclosed herein decrease cross-reactivity and improve sensitivity of the detection.

Antibodies

The disclosure relates generally to antibodies having binding specificity to methotrexate (MTX), and/or MTX conjugated to another molecule. One aspect of the present disclosure is directed to isolated antibodies that bind to MTX. The antibodies may be used in immunoassays that can advantageously detect and quantify amounts of MTX in a biological sample. The immunoassays for measuring MTX in biological samples are rapid, sensitive and accurate, thereby optimizing dosing of MTX during treatment.

In some embodiments, the antibodies can have less than 1% cross-reactivity with DAMPA (4-Amino-4-deoxy-N-10-methylpteroic acid) in a competitive assay. In some embodiments, the antibodies can have less than 1% cross-reactivity with 7-hydroxy-methotrexate (7-OH-MTX) in a competitive assay. In some embodiments, the antibodies can have less than 1% cross-reactivity with folic acid in a competitive assay. In some embodiments, the antibodies can have less than 1% cross-reactivity with folinic acid in a competitive assay.

In certain embodiments, the antibodies of the present disclosure can have less than 2% cross-reactivity with one or more of the following compounds: DAMPA, 7-OH-MTX, folic acid, and folinic acid.

In certain embodiments, the antibodies of the present disclosure can have less than 4% cross-reactivity with one or more of the following compounds: DAMPA, 7-OH-MTX, folic acid, and folinic acid.

In certain embodiments, the antibodies of the present disclosure can have less than 6% cross-reactivity with one or more of the following compounds: DAMPA, 7-OH-MTX, folic acid, and folinic acid.

In certain embodiments, the antibodies of the present disclosure selectively bind MTX and/or MTX conjugated to another molecule and have one or more of the following characteristics: (i) 1% or less cross-reactivity with DAMPA in a competitive assay; (ii) less than 1% cross-reactivity with 7-OH-MTX in a competitive assay; (iii) less than 1% cross-reactivity with folic acid in a competitive assay; (iv) less than 1% cross-reactivity with folinic acid in a competitive assay; (v) less than 1% cross-reactivity with one or more of the following compounds DAMPA, 7-OH-MTX, and folic acid and folinic acid; or (vi) less than 1% cross-reactivity with DAMPA. In certain other embodiments, an antibody selectively binds MTX and/or MTX conjugated to another molecule and has all of the characteristics of (i)-(vi). In still other embodiments, an antibody selectively binds MTX and/or MTX conjugated to another molecule and has both 1% or less cross-reactivity with DAMPA in a competitive assay and less than 1% cross-reactivity with 7-OH-MTX in a competitive assay.

Some antibodies of the present disclosure can have less than 5%, less than 4%, less than 3%, less than 2.5%, less than 2%, less than 1.5% or less than 1% cross-reactivity with one or more of DAMPA, 7-OH-MTX, folic acid, and folinic acid in a competitive assay. In particular, some antibodies can have a cross-reactivity with DAMPA in a competitive assay of 0.5% or less, 0.4% or less, 0.3% or less, or 0.2% or less. In some embodiments, some antibodies can have a cross-reactivity with 7-OH-MTX in a competitive assay of 0.5% or less, 0.4% or less, 0.3% or less, or 0.2% or less.

Some antibodies of the present disclosure can have a sensitivity between 0.01 μM and 0.025 μM.

As stated, the present disclosure provides antibodies or fragments thereof that bind MTX and/or MTX conjugated to another molecule. In some embodiments, the antibodies have a variable heavy chain nucleotide sequence of SEQ ID NO:1. In some embodiments, the antibodies have a variable light chain nucleotide sequence of SEQ ID NO:2. In some embodiments, the antibodies have a variable heavy chain amino acid sequence of SEQ ID NO:3. In some embodiments, the antibodies have a variable light chain amino acid sequence of SEQ ID NO:4. In some embodiments, the antibodies have a variable heavy chain nucleotide sequence of SEQ ID NO:5. In some embodiments, the antibodies have a variable light chain nucleotide sequence of SEQ ID NO:6. In some embodiments, the antibodies have a variable heavy chain amino acid sequence of SEQ ID NO:7. In some embodiments, the antibodies have a variable light chain amino acid sequence of SEQ ID NO:8. In some embodiments, the antibodies have a variable heavy chain nucleotide sequence of SEQ ID NO:9. In some embodiments, the antibodies have a variable light chain nucleotide sequence of SEQ ID NO:10. In some embodiments, the antibodies have a variable heavy chain amino acid sequence of SEQ ID NO:11. In some embodiments, the antibodies have a variable light chain amino acid sequence of SEQ ID NO:12.

In still other embodiments, an antibody or fragment thereof may be a monoclonal or polyclonal antibody. Depending on the methods of preparation, in certain embodiments, the antibodies of the present disclosure can be in a lyophilized state.

The antibodies used in the present disclosure can include immunoglobulin molecules and portions of immunoglobulin molecules capable of binding the desired binding site. The immunoglobulin molecules of the present disclosure can be essentially of any class or isotype (e.g., IgG, IgE, IgM, IgD, IgA and IgY) or subclass (e.g., IgG1, IgG2, IgG3, IgG4, IgA1 and IgA2) of an immunoglobulin molecule. Additionally, structures known as nanobodies and domain antibodies can be used, including polypeptides comprising a single or multiple CDRs of an antibody known to bind the cognate binding site, provided an effective amount of the binding ability is retained.

Generation of Anti-MTX Antibodies

The present disclosure provides a variety of antibodies which selectively bind to methotrexate (MTX) or MTX conjugated to another molecule. These antibodies can be generated by immunizing an animal with a compound having a Formula (1) or equivalents thereof (See Examples 3 and 4). Formula (1) represents the chemical structure of MTX-$N^{10}$—$C_6$—$NH_2$.

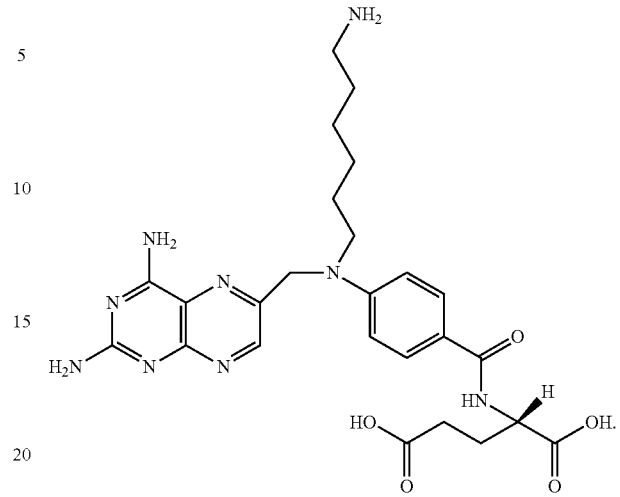

Formula (1)

In some embodiments, an antibody of the present disclosure can be produced by expressing a variable heavy and a variable light chain nucleotide sequence encoded by SEQ ID NO:1 and SEQ ID NO:2, respectively. In certain other embodiments, an antibody of the present disclosure can be produced by expressing a variable heavy and a variable light chain nucleotide sequence encoded by SEQ ID NO:5 and SEQ ID NO:6, respectively. In certain other embodiments, an antibody of the present disclosure can be produced by expressing a variable heavy and a variable light chain nucleotide sequence encoded by SEQ ID NO:9 and SEQ ID NO:10, respectively.

In certain embodiments, an antibody of the present disclosure can be produced by expressing a variable heavy and a variable light chain amino acid sequence encoded by SEQ ID NO:3 and SEQ ID NO:4, respectively. In certain other embodiments, an antibody of the present disclosure can be produced by expressing a variable heavy and a variable light chain amino acid sequence encoded by SEQ ID NO:7 and SEQ ID NO:8, respectively. In some embodiments, an antibody of the present disclosure can be produced by expressing a variable heavy and a variable light chain amino acid sequence encoded by SEQ ID NO:11 and SEQ ID NO:12, respectively.

Enzymes

The present disclosure also discloses methods of detecting methotrexate in a sample using the enzyme dihydrofolate reductase (DHFR) as an alternative to using antibodies. DHFR may be from a recombinant or a naturally occurring source. Using DHFR in the assays may provide additional sensitivity.

In some embodiments, NADPH, the natural cofactor for the reaction catalyzed by DHFR, can be added as a constituent of the assay mixture for optimum binding of methotrexate to DHFR. For increased stability and shelf life, a stable analog of NADPH optionally may be used, with labile phosphate ester bonds replaced with a metabolically stable alternative, including but not limited to imido or methylene linkages.

In some embodiments, the recombinant or naturally occurring DHFR can have less than 4% cross-reactivity with DAMPA (4-amino-4-deoxy-N-10-methylpteroic acid) in a competitive assay. In some embodiments, the recombinant or naturally occurring DHFR can have less than 1% cross-reactivity with 7-hydroxy-methotrexate (7-OH-MTX) in a competitive assay. In some embodiments, the recombinant or naturally occurring DHFR can have less than 1% cross-reactivity with folic acid in a competitive assay. In some embodiments, the recombinant or naturally occurring DHFR can have less than 1% cross-reactivity with folinic acid in a competitive assay.

In certain embodiments, the recombinant or naturally occurring DHFR can have less than 2% cross-reactivity with one or more of the following compounds: DAMPA, 7-OH-MTX, folic acid, and folinic acid.

In certain embodiments, the recombinant or naturally occurring DHFR can have less than 4% cross-reactivity with one or more of the following compounds: DAMPA, 7-OH-MTX, folic acid, and folinic acid.

In certain embodiments, the recombinant or naturally occurring DHFR can have less than 6% cross-reactivity with one or more of the following compounds: DAMPA, 7-OH-MTX, folic acid, and folinic acid.

In certain embodiments, the recombinant or naturally occurring DHFR of the present disclosure selectively bind MTX and/or MTX conjugated to another molecule and have one or more of the following characteristics: (i) 4% or less cross-reactivity with DAMPA in a competitive assay; (ii) less than 1% cross-reactivity with 7-OH-MTX in a competitive assay; (iii) less than 1% cross-reactivity with folic acid in a competitive assay; (iv) less than 1% cross-reactivity with folinic acid in a competitive assay; (v) less than 1% cross-reactivity with one or more of the following compounds DAMPA, 7-OH-MTX, and folic acid and folinic acid; or (vi) less than 4% cross-reactivity with DAMPA. In certain other embodiments, a recombinant or naturally occurring DHFR selectively binds MTX and/or MTX conjugated to another molecule and has all of the characteristics of (i)-(vi). In still other embodiments, a recombinant or naturally occurring DHFR selectively binds MTX and/or MTX conjugated to another molecule and has both 4% or less cross-reactivity with DAMPA in a competitive assay and less than 1% cross-reactivity with 7-OH-MTX in a competitive assay.

In some embodiments, recombinant or naturally occurring DHFR can have 6% or less, 5% or less, 4% or less, 3% or less, 2.5% or less, 2% or less, 1.5% or less, or 1% or less cross-reactivity with one or more of DAMPA, 7-OH-MTX, folic acid, and folinic acid in a competitive assay. In some embodiments, recombinant or naturally occurring DHFR can have a cross-reactivity with DAMPA in a competitive assay of 6% or less, 5% or less, 4% or less, 3% or less, 2.5% or less, 2% or less, 1.5% or less, or 1% or less. In other embodiments, recombinant or naturally occurring DHFR can have a cross-reactivity with 7-OH-MTX in a competitive assay of 1.5% or less, 1% or less, or 0.5% or less. In some embodiments, recombinant or naturally occurring DHFR can have 1.5% or less, 1% or less, or 0.5% or less cross-reactivity with DAMPA in a competitive assay. In some embodiments, recombinant or naturally occurring DHFR can have 1.5% or less, 1% or less, or 0.5% or less cross-reactivity with folic acid in a competitive assay. In other embodiments, recombinant or naturally occurring DHFR can have 1.5% or less, 1% or less, or 0.5% or less cross-reactivity with folinic acid in a competitive assay.

In some embodiments, recombinant or naturally occurring DHFR can have a sensitivity between 0.0015 µM and 0.0025 µM.

Assay Development and Methods

The antibodies and enzymes disclosed herein may be used in various formats of assays and methods that measure, quantify, and/or detect the presence of MTX in a sample. In some embodiments, a competitive assay format is used. Antibodies or enzymes may be attached to a solid support and are used to capture labeled and unlabeled MTX (when present in the sample). In the absence of methotrexate in the sample, the labeled methotrexate will bind to the antibody/enzyme on the solid support, generating an electrochemiluminescent (ECL) signal. Free methotrexate in the sample will compete with the labeled methotrexate for the antibody/enzyme binding site, resulting in a decrease in ECL signal. ECL signal is inversely proportional to the binding of the unlabeled MTX from the sample.

The antibodies and enzymes described herein can be combined with a sample to perform the assays. The sample may be a biological sample, such as tissue extracts, tissues used in immunohistochemistry, or fluids. The fluid samples may be derived from blood, plasma, serum, or buffer.

The antibodies and enzymes described herein may be linked or bound to various components or moieties in order to perform assay functions. For example, in some embodiments, the antibodies and enzymes discussed herein may be bound directly through covalent or non-covalent attachment, or indirectly to a solid support or carrier to form a capture molecule. When bound indirectly, intermediate linkers may be used to bind the components. Suitable intermediate linkers include, but are not limited to, an amino group or a carboxylate group, biotin, ligands, or other chemical bonds. Suitable solid supports or carriers include, but are not limited to, glass surfaces (e.g., a glass slide or bead), plastic surfaces, metal surfaces, polystyrene surfaces (e.g., a bead or a plate), nitrocellulose surfaces, microparticles, nano-particle surfaces, plates, wells, disposable ECL electrodes, and paramagnetic or magnetic beads that may be coated with avidin or streptavidin or have other surface functionalities to promote binding affinity.

In some embodiments, labeled MTX is used in the competition assay format. In certain embodiments, some of the methotrexate may be linked or bound, directly through covalent or non-covalent attachment, or indirectly, to a label to form a labeled MTX. When bound indirectly, intermediate linkers may be used as discussed herein.

As stated, in some embodiments, an antibody or fragment thereof or DHFR may be bound to a solid support to form a capture molecule during an assay or method of the present disclosure. This binding can be performed prior to contacting the antibody or fragment thereof or DHFR with the sample or after. The antibody or fragment thereof or DHFR can be bound to a solid support directly (e.g., covalently) or indirectly (e.g., using binding partners).

Similarly, in some embodiments, a MTX molecule may be bound to a label to form a labeled MTX during an assay or method of the present disclosure. This binding can be performed prior to contacting the MTX molecule with the sample or after. The MTX molecule can be bound to a label directly (e.g., covalently) or indirectly (e.g., using binding partners).

Examples of suitable binding partners include, but are not limited to, biotin/streptavidin; antibody/antigen; antibody/Fc receptor; an antibody of a first species and an antibody of a second species against first species antibodies; Fc/Fc receptor; 6-His/Ni$^{2+}$; 6-His/cobalt; and 6-His/divalent cation resin.

In other embodiments, a binding pair that binds binding partners can be streptavidin and biotin or two antibodies that bind each other such as an antibody that binds an Fc portion of another antibody. In other embodiments, the binding may occur through the interaction of numerous binding pairs. In still other embodiments, each component can be a corresponding member of a binding pair. It is contemplated that essentially any method can be used that results in the binding of the antibody to the solid support or the MTX molecule to a label, e.g., directly or indirectly. In some embodiments, an antibody comprises biotin and a solid support comprises streptavidin or vice versa.

In some embodiments, the label may be any label that corresponds to a suitable detection method. Suitable detection moieties include, but are not limited to, electrochemiluminescence labels or compounds, chemiluminescent compounds, enzyme labels, fluorophores, chromogenic compounds, radiolabels, catalysts, colorimetric compounds or labels, labeled antibodies, latex particle, a magnetic particle, a radioactive element, fluorescent dyes, phosphorescent dyes, dye crystalites, gold particles, silver colloidal particles, selenium colloidal particles, metal chelates, coenzymes, electro active groups, oligonucleotides or stable radicals. The metal chelate may be a ruthenium, an osmium metal chelate or a europium chelate. The detection method may include any known detection method including, but not limited to, chromogenic, radioisotopic, fluorescence, immunofluorescence, luminescence, bioluminescence, and electrochemiluminescence (ECL).

In some embodiments, the detection method may be electrochemiluminescence (ECL). An electrochemiluminescent compound may serve as the label that may be detected or quantified within an ECL reaction chamber, such as in a flow cell, or on a disposable electrode. The solid support may serve to hold the antibody bound to the label near an ECL electrode in the ECL reaction chamber during detection.

Electrochemiluminescence (ECL) is the process whereby a molecular species, such as an "ECL label," luminesces upon the exposure of that species to electrochemical energy in an appropriate surrounding chemical environment. ECL is a rapid and sensitive bio-analytical detection technique that is a regenerative process. Some of the advantages achieved with ECL as a detection method in biological sample analysis include simpler, less expensive instrumentation; stable, nonhazardous labels; and increased assay performance characteristics such as lower detection limits, higher signal to noise ratios, and lower background levels. As a detection method in clinical sample analysis, ECL also has the advantage of greater sensitivity and specificity. Certain applications of ECL have been developed and reported in the literature. U.S. Pat. Nos. 5,147,806, 5,068,808, 5,061,445, 5,296,191, 5,247,243, 5,221,605, 5,238,808, 5,310,687, 5,714,089, 6,165,729, 6,316,607, 6,808,939, 6,881,589, 6,881,536, and 7,553,448, the disclosures of which are incorporated herein by reference, detail certain methods, apparatuses, chemical moieties, inventions, and associated advantages of ECL.

Electrochemiluminescence signals are generated by a redox reaction between an electrochemiluminescent label, such as an ECL-active label with a redox substrate that occurs at the surface of an electrode. In certain embodiments, the ECL label is a ruthenium(Ru)-containing reagent. One example of a suitable electrochemiluminescent label is Tris(bypyridine)ruthenium(II) ([Ru(bipy)3]$^{2+}$), also referred to as TAG. In some embodiments, the redox substrate is tripropylamine (TPA).

In some embodiments, a magnet usually positioned below an electrode may attract the magnetic beads, pulling down the Ru-labeled complex near the electrode. In some embodiments, the ECL reaction can occur in an ECL analyzer. The Ru may then be oxidized. Oxidized tripropylamine (TPA) may react with the oxidized Ru, which then may emit a photon. The redox reaction between Ru and the redox substrate tripropylamine (TPA) that occurs only in the electric field near the electrode may be a regenerative process during continued application of voltage, which allows for an ECL signal that undergoes amplification over time. Because photons can only be generated near the electrode surface, electrochemiluminescence only occurs when the Ru is brought into proximity with the electrode by the magnet, thereby reducing background levels. Nonspecific ECL is not triggered by any known natural constituents of biological samples; therefore, unlike chemiluminescence, which often displays background artifacts due to nonspecific triggering of chemiluminescent detection moieties, ECL maintains reduced background levels.

In some embodiments, the solid support and/or the label may be from a lyophilized composition that is rehydrated with the sample for use in an assay. The lyophilized composition may contain standard and/or other necessary assay specific components of an assay, such as buffers, reagents, detergents, preservatives, salts, proteins, antibodies, etc. It is contemplated that the solid support and the label may be lyophilized in separate compositions, and then rehydrated with the sample. It is also contemplated that the solid support and the label may be lyophilized in the same composition, and then rehydrated with the sample.

The antibodies and enzymes of the present disclosure may be used in various assay formats, including, for example, enzyme-linked immunosorbent assays (ELISA) or ECL assays for detecting the presence of MTX. In one aspect of the present disclosure, the assay method steps for detecting and/or quantifying methotrexate (MTX) in a sample may include combining in a solution the sample with a capture molecule and a labeled MTX, wherein the capture molecule is capable of binding the labeled MTX, and wherein MTX, when present in the sample, competes with the labeled MTX for binding to the capture molecule; and detecting an amount of labeled MTX bound to the capture molecule through signal produced by a label on the bound labeled MTX, wherein the signal is inversely proportional to the amount of MTX present in the sample.

In some embodiments, the capture molecule comprises an antibody or fragment thereof attached to a solid support. In some embodiments, a capture molecule can be an antibody or fragment thereof attached to a solid support, where the antibody or fragment thereof binds MTX and/or MTX conjugated to another molecule(s). For example, the antibody may selectively bind to a molecule conjugated to MTX as compared to the same molecule without conjugation to MTX. When an antibody is described as binding to MTX it is understood that this also includes an antibody that selectively binds a molecule conjugated to MTX as compared to the same molecule without conjugation to MTX.

In some embodiments, the capture molecule comprises DHFR from a recombinant or naturally occurring source attached to a solid support. It is contemplated that other sources of DHFR may be used as well.

In some embodiments, the labeled MTX comprises a methotrexate (MTX) molecule, or MTX conjugated to another molecule, covalently linked to a label. In some embodiments, the labeled MTX comprises a MTX conjugate covalently linked to a label.

In some embodiments, the conjugate of MTX is a MTX derivative modified at the $N^{10}$ position. In some embodiments, the conjugate of MTX is a MTX derivative modified at the gamma ($\gamma$)-position of the carboxyl group of MTX either chemically or naturally.

It is contemplated that the steps of the methods of the present disclosure do not have to be completed in the order provided herein, and may be performed in different orders. Additionally, the sample may be incubated for a period of time before a washing step and removal of any unbound or excess materials. It is further contemplated that additional washing steps to remove materials during the assay may be performed at additional times during the method, such as after the addition of each assay component and/or before the detecting step.

In other embodiments, a capture molecule and sample are combined prior to the addition of a labeled MTX. For example, a solution comprising a sample and a capture molecule may be incubated for a period of time prior to the addition of a labeled MTX.

Components/reagents used in embodiments of the assays disclosed herein can be lyophilized using standard lyophilization methods. For example, the components and reagents can be lyophilized by creating a solution containing the desired component(s), such as a labeled MTX or capture molecule. Then the solution can be used to form drops that are allowed to fall into a freezing medium (e.g., liquid nitrogen), typically forming frozen spheres, and then lyophilizing the frozen spheres or pellets.

In some embodiments of the assays, a lyophilized composition containing a capture molecule or a labeled MTX or both is rehydrated with the sample. This embodiment may be advantageous in that the sample is essentially undiluted during the assay, which may result in higher levels of sensitivity because more MTX is present in an undiluted sample as compared to a diluted sample of the same volume. In some embodiments, a sample is diluted prior to combining with the other reagents. In some embodiments, a sample is not diluted prior to combining with the other reagents.

Kits

Another aspect of the present disclosure is directed to kits for performing the methods described herein. For example, a kit may be used for detecting MTX in a sample. Materials to be included in the kit may vary depending on the ultimate purpose. As such, the kits may include one or more components that are used in the methods. The kits disclosed herein may include at least one component selected from the following components: a solid support, an antibody specific for MTX, a recombinant or naturally occurring DHFR enzyme, a labeled MTX, assay reagents, necessary buffers, standards and instructions for performing the methods disclosed herein, as well as other components and elements of the methods described herein. The standards can be additional chemical reagents or data (empirical) in printed or electronic form necessary for the calibration needed for performance of the assay. The kit may also include the use of an analyzer instrument, such as an ECL analyzer, and include instructions for use and related instrument components, such as cartridges used with the analyzer instrument.

The present disclosure can be better understood by reference to the examples included herein, which illustrate but do not limit the present teachings described herein. It is to be understood that both the descriptions disclosed herein are examples only. The examples are merely illustrative and intended to be non-limiting. Moreover, it should be understood that various features and/or characteristics of differing embodiments herein may be combined with one another. It is therefore to be understood that numerous modifications may be made to the illustrative embodiments and that other arrangements may be devised without departing from the scope of the present disclosure. Other embodiments will be apparent to those skilled in the art from consideration of the disclosure and practice of the various example embodiments disclosed herein. It is intended that the specification and examples be considered as examples only, with the true scope of the invention being indicated by the claims.

EXAMPLES

The following examples are intended to be non-restrictive and explanatory only.

Antibody Assay Examples

Example 1—Preparation of Modified MTX

A modified MTX with the chemical structure MTX-$N^{10}$—$C_6$—$NH_2$(Formula 1) was synthesized as shown in FIG. 1. The product was a MTX derivative modified at the position 10 nitrogen)($N^{10}$ with a 6-carbon linker.

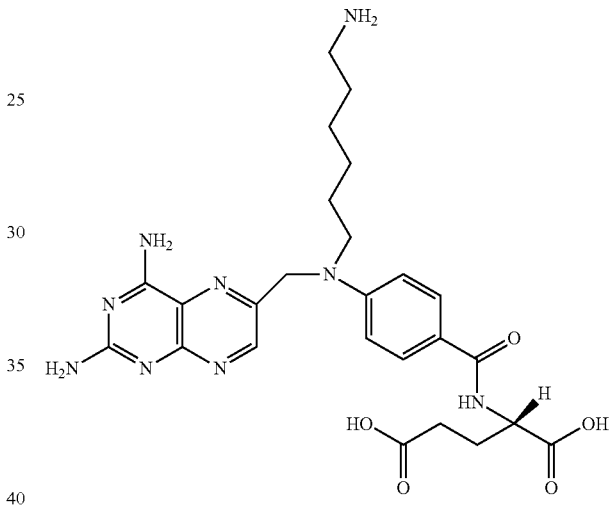

Formula (1)

In Step [2] of the scheme in FIG. 1, N-(p-aminobenzoyl)-L-glutamic acid diethyl ester (1.45 g, 4.5 mmol) was mixed with 4.6 mL of N,N-dimethylformamide (DMF) & 1.8 mL of diisopropylethylamine (DIPEA) and stirred at room temperature (RT). To the above mixture was added 1.37 g (1.15 mL) of 4-(boc-amino) hexyl bromide and stirred at 58° C. for 3 days. After 3 days, the resulting mixture was diluted with 180 mL of ethyl acetate (EtOAc) and washed with 2×100 mL of water. The organic layer was dried over sodium sulfate, concentrated and purified by a flash column employing EtOAc/hexanes (6/4) as eluent. The desired product was recrystallized from EtOAc/Hexanes to yield 1.12 g of compound.

In Step [2a], 2,4-diamino-6-(hydroxymethyl)pteridine hydrobromide (1.0 g) was mixed with 20 mL of thionyl bromide and the mixture was stirred at room temperature (RT) for 24 hr. The solvent was evaporated and solid was washed with 300 mL of dry toluene to yield 1.62 g of brown solid. The product was used in the next step without further purification.

In Step [3], the product from Step [2] (85 mg) was mixed with 0.9 mL of DIPEA and 0.6 g of Step [2a] in 3 mL of dimethylacetamide (DMA) and stirred at 62° C. for 15 h. The resulting mixture was filtered, washed with dichloromethane (DCM) and concentrated under reduced pressure. The concentrated product was redissolved in 150 mL chloroform and washed with water, filtered over $Na_2SO_4$ and dried. The solid was purified by a prep plate employing 5% methanol in DCM as eluent to yield 15 mg of desired product.

In Step [4], the product from Step [3] (12 mg) was mixed with 3 mL of ethanol and 0.08 mL of 4N NaOH was added. The resulting mixture was stirred at RT for 18 hr. The solvent was removed under reduced pressure. 15 mL (2×) of DCM was added and concentrated under reduced pressure. The product was used in the next step without further purification.

In Step [5], the product of Step [4] (11 mg) was mixed with 4 mL of 40% trifluoroacetic acid (TFA) in DCM. The resulting mixture was stirred at RT for 2 hr. The solvent was removed under reduced pressure. DCM (20 mL) was added and removed. The end product formed is the compound shown in Formula (1) and is also referred to as MTX-$N^{10}$—$C_6$—$NH_2$ herein. This product was used to conjugate with KLH for immunization of mice to generate the antibodies of the present disclosure.

This product, Formula (1), was also used to prepare labeled MTX. Formula (1) was conjugated to TAG as shown in Step [6] of FIG. 1. In Step [6], the product of Step [5] (3 mg) was dissolved in 0.5 mL 0.2N carbonate-bicarbonate buffer (pH 9.4). TAG-NHS ester (~3 mg, 3×500 nmol) was dissolved in 0.2N carbonate-bicarbonate buffer (3×80 □L) and was added to the above mixture. The reaction mixture was stirred for 1 hr. at RT. HPLC was used to purify the desired product employing 0.1N TEAA/acetonitrile as eluents. The product of the synthesis was confirmed by MS Spectrum and NMR analysis.

Example 2—Conjugation of MTX-$N^{10}$—$C_6$—$NH_2$ to KLH for Immunization

MTX was conjugated to KLH by cross-linking the MTX-$N^{10}$—$C_6$—$NH_2$ and KLH with glutaraldehyde.

For the preparation of MTX-$N^{10}$—$C_6$—$NH_2$—KLH, 4.3 mg KLH (reconstituted in sodium bicarbonate buffer) was mixed with 0.315 mg MTX-$N^{10}$—$C_6$—$NH_2$ (reconstituted in DMSO). The mixture was treated (while slowly mixing) with glutaraldehyde to a final concentration of 1.0%. The cross linking reaction was allowed to proceed for 3 hours at 2-4° C. The reaction was stopped by adding 25 mg of sodium cyanoborohydride to a final concentration of 10 mg/mL for 1 hour at 2-4° C. After the conjugation, MTX-$N^{10}$—$C_6$—$NH_2$-KLH was dialyzed into phosphate buffered saline (PBS) pH 7.4. Protein concentration was determined by bicinchoninic acid (BCA) assay.

Example 3—Immunization of Balb/c Mice with MTX-N10-C6-KLH Conjugate

The immunogen was prepared by emulsifying MTX-$N^{10}$—$C_6$-KLH in Complete Freund's Adjuvant (CFA) and Incomplete Freund's Adjuvant (IFA) for primary immunization and booster immunizations, respectively. Emulsions were prepared by mixing antigen and adjuvant by pushing the mixture repeatedly through an emulsifying needle.

For the primary immunization, a group of 16 female 5-6 week old Balb/cAnNHsd mice was immunized intraperitoneally with 50 μg of MTX-$N^{10}$—$C_6$-KLH emulsified in Complete Freud Adjuvant (CFA) in a total volume of 0.2 mL. Mice received booster immunizations on days 15, 28 and 42, subcutaneously containing 25 μL of MTX-$N^{10}$—$C_6$-KLH emulsified in Incomplete Freud Adjuvant (IFA).

To analyze the anti-MTX antibodies in the mice, serum samples were taken on day 60. Antibody responses (titer) were determined with a biotinylated MTX-$N^{10}$—$C_6$-BSA conjugate pre-coated beads and TAG conjugated goat anti-mouse IgGγ. Samples were analyzed at various dilutions in the MTX antibody assay buffer containing 1×PBS, 0.5% of BSA, 0.3% Tween® 20 and 0.1% methylisothiazolinone (MIT). Mice with the highest response were selected for use in hybridoma generation.

Example 4—MTX Hybridoma Generation

Once the desired antibody responses were induced in mice, B cell hybridomas were generated with the splenic cells isolated from selected mice. Typically, a mouse was given 3 pre-fusion booster immunizations with MTX-$N^{10}$—$C_6$-KLH in PBS i.p. at days 3, 2 and 1 before its spleen was harvested for generating hybridomas.

Spleens were removed from animals and teased through a 70 μm cell strainer to release the splenocytes. Splenocytes were washed once with DMEM and layered on top of Lympholyte M (Cedarlane Labs) density separation medium in a 50 mL tube. The gradient was centrifuged at room temperature for 20 minutes at 1500×g. Splenocytes (depleted of erythrocytes, dead cells and debris) were collected from the interface between the Lympholyte M and the DMEM. The recovered cells were washed once with DMEM.

P3X mouse myeloma cells were processed using the same density gradient separation procedure. Cell counts for the P3X myeloma cells and the splenocytes were obtained using the trypan blue exclusion method and a hemacytometer.

The splenocytes and myeloma cells were mixed at a 3:1 ratio (splenocytes:myelomas) and centrifuged to pellet the cells. Cell fusion was performed by adding 1 mL of 50% polyethylene glycol 1500 (PEG, Roche Applied Science) to the pelleted cells drop-wise over 1 minute with gentle shaking. After addition of the PEG, the mixture was incubated for 1 minute with gentle shaking. DMEM (10 mL) was added slowly over approximately 5 minutes followed by incubation for 10 minutes at 37° C. in a water bath. DMEM (20 mL) was added and cells were pelleted by centrifugation at 200×g for 5 minutes at room temperature. The cell pellet was resuspended in growth media [DMEM (Lonza) supplemented with 15% heat inactivated Fetal Bovine Serum (Life Technologies), 4.0 mM L-Glutamine (Lonza), 2.0% Hybridoma Fusion and Cloning Factor (Roche Applied Science), 1% Penicillin/Streptomycin solution (Lonza), 1.0% OPI (Oxaloacetate, Pyruvate, Insulin) (Sigma) and 1.0 ng/mL mouse recombinant IL-6 (Life Technologies)] at a concentration of 5.0×105 cells/mL. Cells were transferred to 96-well plates (100 μl per well [50,000 cells/well]) and incubated at 37° C. with 5.0% $CO_2$.

After 18-30 hours 100 μl per well of growth media containing 2× Hypoxanthine, aminopterin, thymidine (HAT) solution (Life Technologies) was added to each well. The 96-well plates were incubated for approximately 10 days at 37° C. with 5% $CO_2$. When approximately 10% of the wells began turning yellow, 100 μl of media was removed and replaced with 100 μl of fresh 1×HAT media. Each well was sampled 3-4 days after the media exchange. Samples were tested using electrochemilumiescence (ECL) to screen for wells containing hybridomas positive for antibodies against methotrexate. Hybridomas positive for anti-methotrexate antibodies were expanded to 24-well plates followed by expansion to T25 flasks. Cells were cryopreserved using growth media supplemented with 10% DMSO. Cultures containing cells with desirable traits were cloned 3 times by limiting dilution to ensure all cells were derived from a single cell.

Example 5—Fusions for Hybridoma Generation

Three fusions were performed using the procedures described above. The results are shown in Table 1.

TABLE 1

|  | Fusion | | |
| --- | --- | --- | --- |
|  | 1 | 2 | 3 |
| Mouse # used for fusion | 1 | 3 | 6&8 |
| Fusion day (# days post-primary immunization) | 76 | 90 | 217 |
| Number of 96-well fusion plates | 7 | 15 | 25 |
| Plate numbers | 1-7 | 8-22 | 23-47 |
| Number of hybridomas selected for further evaluation | 7 | 9 | 6 |
| Hybridomas selected for further evaluation | 3A7, 3B7, 4G4, 5B6, 6E11, 6D4, 6F3 | 9E1, 10C7, 11C9, 11H3, 14A4, 14B11, 15H10, 18B10, 19A6 | 40A8, 40A10, 40D9, 40E2, 43B2, 45C11 |

Based on performance in MTX screening and competition assays and as a result of a cross-reactivity analysis with MTX metabolites and related compounds, four hybridomas (6D4, 10C7, 19A6, 45C11) were selected for further evaluation in the quantitative methotrexate assay.

Example 6—MTX Antibody Cross-Reactivity to Metabolites and Related Compounds

The 4 selected MTX antibodies, 10C7, 45C11, 6D4, 19A6, were evaluated for cross-reactivity with MTX metabolites and related compounds (7-OH-MTX, DAMPA, Folic Acid and Folinic Acid). The amount of cross-reactivity with each chemical is defined as the percent ratio of the calculated MTX concentration of the chemical divided by 100 µM, which was the spiked concentration of the chemical. The percent cross-reactivity with each chemical is summarized in Table 2.

TABLE 2

MTX Antibody Cross-Reactivity with Metabolites and Related Compounds

| | % Cross-Reactivity | | | |
| --- | --- | --- | --- | --- |
| Chemicals | mAb 10C7 | mAb 45C11 | mAb 6D4 | mAb 19A6 |
| 7-OH-MTX | 0.37 | 0.090 | 0.91 | 0.76 |
| DAMPA | 0.43 | 38.9 | 0.52 | 0.029 |
| Folic Acid | 0.24 | 0.082 | 0.48 | 0.073 |
| Folinic Acid | 0.28 | 0.074 | 0.24 | 0.11 |

All MTX antibodies had <1.0% cross-reactivity with 7-OH-MTX, DAMPA, folic acid and folinic acid except antibody 45C11 which had 38.9% cross-reactivity with DAMPA.

Example 7—Quantitative Methotrexate Assay Method Using Antibody 45C11

A set of frozen calibrators (MTX at concentrations of 0 to 1,000 µM) were obtained from a −80° C. freezer for each assay plate. The calibrators were allowed to equilibrate at room temperature for 20-30 minutes. The plate was placed onto the Thermostat plate shaker preset to 37±2° C. 50 µL of each calibrator was added in triplicate directly into plate wells. 25 µL of MTX detector reagent (MTX-$N^{10}$—$C_6$-TAG) was added into each assay well. 25 µL of MTX capture reagent (Bi-45C11 Ab attached to streptavidin superparamagnetic beads) was added to each well containing calibrator. The Thermostat plate shaker was turned on and set at 900 rpm for 1 minute±30 seconds to mix. The assay plate was sealed with a plate sealer and the plate was left on the Thermostat shaker for 45±1 minute without shaking.

The assay plate was washed two times with 150 µL/well of Wash Buffer according to the following procedure: (1) The magnetic beads were pelleted in each plate well by placing the plate on a plate magnet for 2±0.5 min (2) The liquid was removed from the wells of the plate by inversion into an appropriate waste container while holding the assay plate on the magnet. The residual liquid was removed by inverting the plate and patting the plate against a stack of paper towels to blot any excess liquid. (3) 150 µL/well of Wash Buffer was added to each plate well. (4) The assay plate was re-suspended and washed by placing the plate on a MicroMix plate shaker set at Form 8 and Amp 6 for 2±0.5 minutes. Steps (1)-(4) were repeated one additional time.

Figure 2:
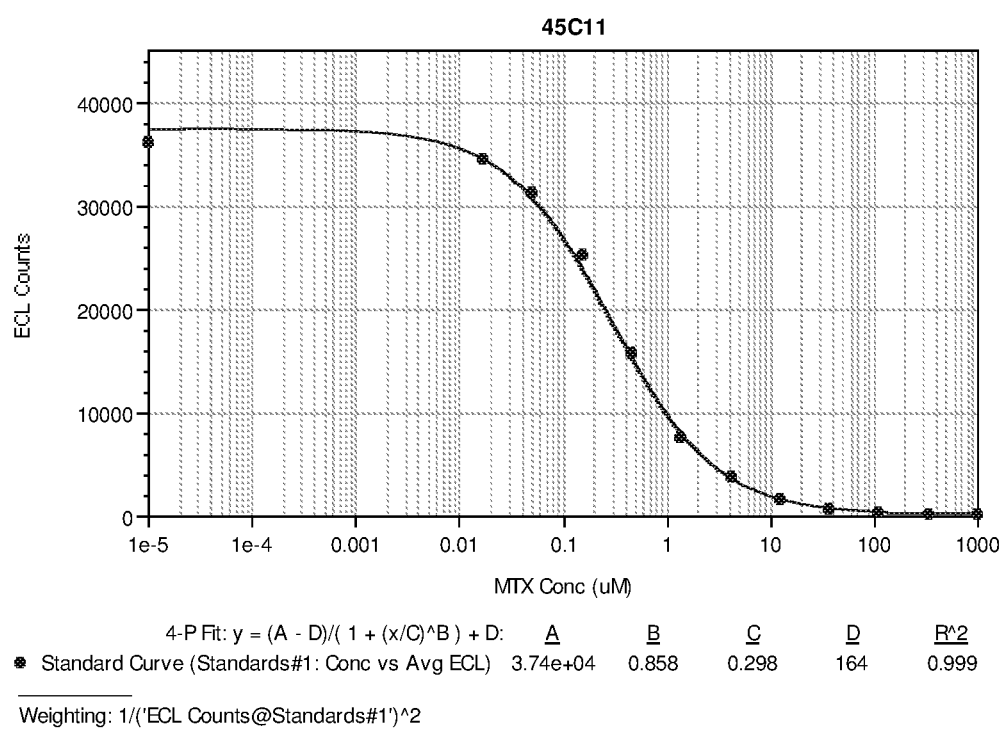
FIG. 2 is a curve showing the dynamic range of an assay of the present disclosure.

100 µL/well of Wash Buffer was added to re-suspend the beads. The assay plate was read on an ECL analyzer with a 50 µL draw volume. Increasing amounts of calibrator (unlabeled MTX) in the human plasma competed with TAG-labeled MTX for binding to the antibody. The ECL signal was inversely proportional to the amount of calibrator bound to the antibody. Results are shown in Table 3. A curve showing the dynamic range of the assay is illustrated in FIG. 2 (45C11).

TABLE 3

| MTX Conc. (µM) (n = 3) | Avg. ECL | ECL CV % | Avg. Conc. | % AR |
| --- | --- | --- | --- | --- |
| CAL1 (0) | 36098 | 4.1 | NA | NA |
| CAL2 (0.017) | 34477 | 4.6 | 0.018 | 103 |
| CAL3 (0.051) | 31170 | 5.6 | 0.047 | 92 |
| CAL4 (0.152) | 25193 | 3.4 | 0.13 | 85 |
| CAL5 (0.457) | 15745 | 4.7 | 0.439 | 96 |
| CAL6 (1.37) | 7700 | 4.3 | 1.479 | 108 |
| CAL7 (4.12) | 3737 | 9.6 | 4.12 | 100 |
| CAL8 (12.35) | 1599 | 9.1 | 12.81 | 104 |
| CAL9 (37.04) | 763 | 7.8 | 36.42 | 98 |
| CAL10 (111.11) | 406 | 8.4 | 107.07 | 96 |
| CAL11 (333.33) | 254 | 2.7 | 337.19 | 101 |
| CAL12 (1000) | 197 | 0.7 | 1091 | 109 |

% AR—Percent Analytical Recovery

Example 8—Quantitative Methotrexate Assay Method Using Antibody 10C7

Figure 3:
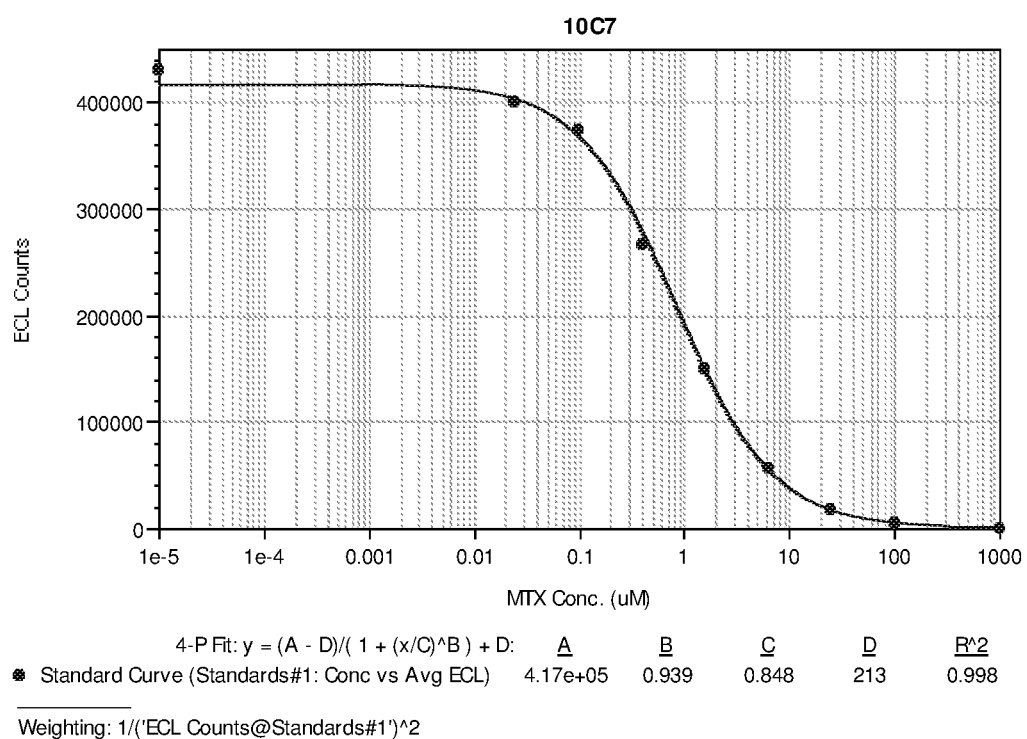
FIG. 3 is a curve showing the dynamic range of an assay of the present disclosure.

The assay protocol used was the same as in Example 7. Increasing amounts of calibrator (unlabeled MTX) in the human plasma competed with TAG-labeled MTX for binding to the antibody. The ECL signal was inversely proportional to the amount of calibrator bound to the antibody. Results are shown in Table 4. A curve showing the dynamic range of the assay is illustrated in FIG. 3 (10C7).

TABLE 4

| MTX Conc. (μM) (n = 3) | Avg. ECL | ECL CV % | Avg. Conc. | % AR |
|---|---|---|---|---|
| CAL1 (0.0) | 429802 | 0.8 | NA | NA |
| CAL2 (0.0245) | 400908 | 1.8 | 0.0281 | 115 |
| CAL3 (0.0977) | 373863 | 1.8 | 0.0855 | 88 |
| CAL4 (0.3906) | 266154 | 3.9 | 0.4655 | 119 |
| CAL5 (1.5625) | 150157 | 1.5 | 1.5688 | 100 |
| CAL6 (6.25) | 55931 | 5.6 | 6.2325 | 100 |
| CAL7 (25) | 18434 | 5.4 | 22.7702 | 91 |
| CAL8 (100) | 4601 | 6.8 | 107.8217 | 108 |
| CAL8 (1000) | 763 | 7.6 | 1000.1278 | 100 |

% AR—Percent Analytical Recovery

DHFR Assay Examples

Example 9—Preparation of Biotinylated Dihydrofolate Reductase (DHFR)

Recombinant dihydrofolate reductase (DHFR) (Sigma Cat: D6566-0.25UN) was buffer exchanged into DHFR conjugation buffer (10.5 mM $KH_2PO_4$, 139.5 mM $K_2HPO_4$ and 150.6 mM NaCl, pH 7.7-7.9 (pH 7.8) freshly added with 0.5 mM dithiothreitol (DTT), 1.0 mM ethylenediaminetetraacetic acid (EDTA) and 5 μM NADPH).

The DHFR was biotinylated with EZ-Link Sulfo-NHS-LC-Biotin (Thermo Cat: 21327) in the DHFR conjugation buffer at a molar challenge ratio of 1:5 (DHFR: EZ-Link Sulfo-NHS-LC-Biotin). Bi DHFR was stored in 50% glycerol.

Example 10—Preparation of TAG γ-$C_3$-MTX

Figure 4:
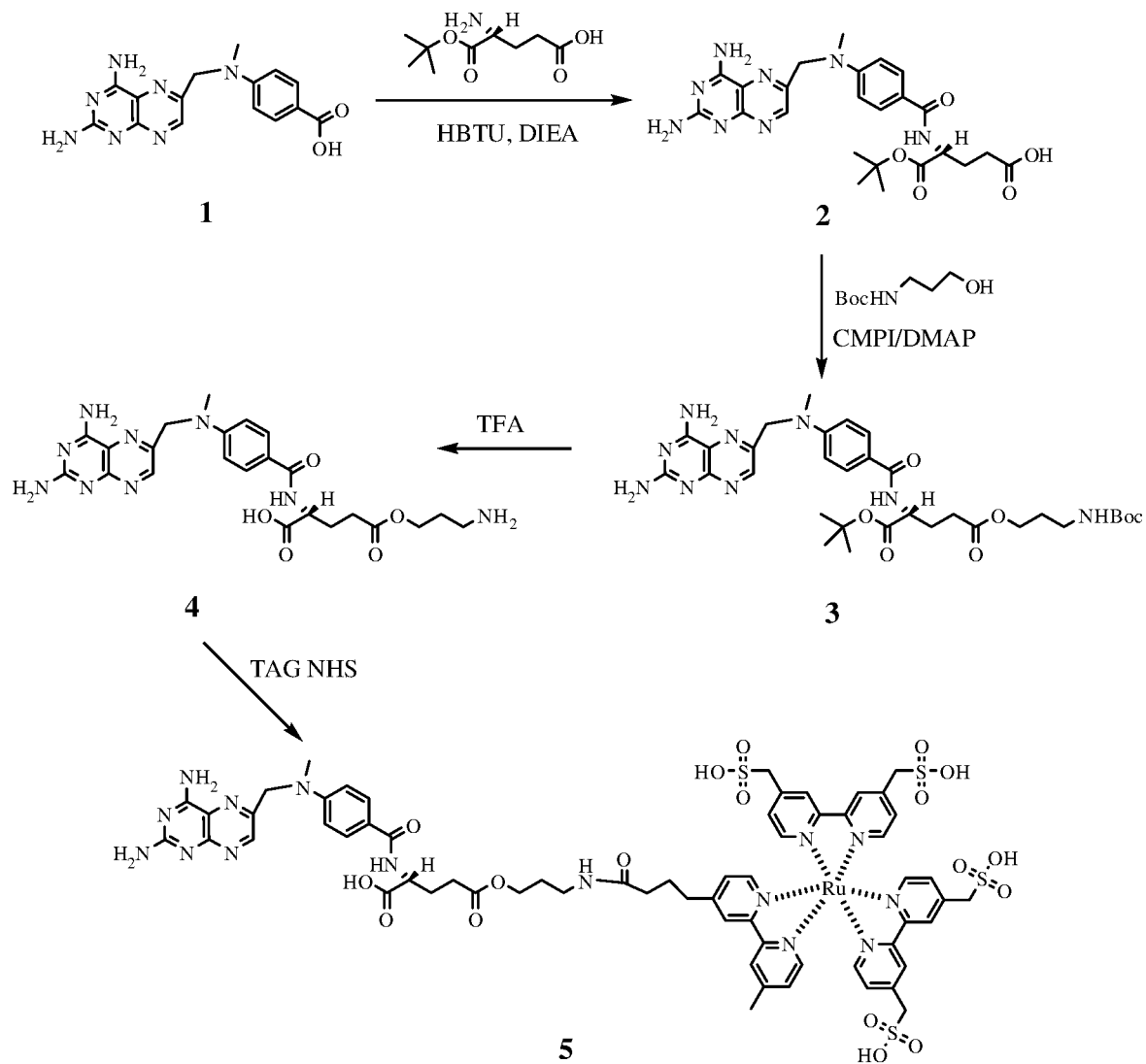
FIG. 4 is a schematic of a chemical synthesis of the present disclosure.

TAG γ-$C_3$-MTX was chemically synthesized as shown in FIG. 4. In Step [2] of the scheme 4-[[(2,4-Diamino-6-pteridinyl)methyl]methylamino]-Benzoic acid (33 mg) was mixed with 38 mg of HBTU (N,N,N',N'-Tetramethyl-O-(1H-benzotriazol-1-yl) uronium hexafluorophosphate) and 12.9 mg of DIEA (N,N-Diisopropylethylamine) in 4 mL DMF (Dimethylformamide). The resulting mixture was stirred at room temperature under Argon. To the above mixture was added 20.3 mg of L-Glu(OH)-OtBu in 3 mL of N,N-dimethylformamide and stirred at RT for 2 hr. under Argon. The solvent was removed under reduced pressure. 10 mL (2×) of dichloromethane was added and removed under reduced pressure.

In Step [3], the product from Step [2] (33 mg) in DMF was added to 3-(Bocamino)-1-propanol (20 mg), 2-Chloro-1-methylpyridinium iodide (CMPI, 18 mg) & 4-dimethyl-aminopyridine (DMAP, 18 mg) in 2 mL DMF. The resulting mixture was stirred at RT under Argon for 6 hr. The solvent was evaporated and the resulting mixture was redissolved in 50 mL of DCM, washed with water, dried over $Na_2SO_4$ and concentrated. The product was purified over a prep plate employing 5% methanol in DCM as eluent to yield 8.5 mg of product.

In Step [4], the product from Step [3] (6 mg) in 3 mL of 50% trifluoroacetic acid in DCM was stirred at RT for 2 hr. The solvent was removed under reduced pressure. 10 mL (2×) of DCM was added and removed under reduced pressure.

In Step [5], the product from Step [4] (3.4 mg) was dissolved in 0.42 mL of water and 1.0 mL of 0.2N carbonate-bicarbonate buffer (pH9.4) was added. TAG-NHS ester (~11 mg, 11×500 nmol) was dissolved in 0.2N carbonate-bicarbonate buffer (11×50 μL) and was added to the above mixture. The reaction mixture was stirred for 1 hr. at RT. HPLC was used to purify the desired product using 0.1N TEAA/acetonitrile as eluents. The product was confirmed by MS.

Example 11—Assay Buffer and Reagents

The DHFR assay buffer was MTEN buffer [50 mM MES (2-(N-Morpholino)ethanesulfonic acid)/25 mM Tris/25 mM ethanolamine/100 mM NaCl, pH 5.5] with 0.10% Tween-20 and 0.5% BSA. NADPH was added fresh to 5.0 μM final concentration.

Assay capture reagent (Bi DHFR pre-bound to M280-SA beads) was prepared by incubating Bi DHFR and M280-SA beads at a ratio of 5.0 μg of Bi DHFR per mg of M280-SA beads at 2-8° C. for 1 hour with gentle mixing. The beads were washed 3 times in DHFR assay buffer.

Assay detector reagents were prepared in DHFR assay buffer.

Example 12—the Requirement of NADPH

NADPH is known as a co-factor for the binding of MTX and DHFR. Capture reagent was incubated in 75 μL of DHFR assay buffer without NADPH, and with 1.0 and 5.0 μM NADPH. Two fold TAG γ-C3-MTX serial dilutions were prepared in buffer with 0.0, 1.0 and 5.0 μM NADPH. 25 μL of TAG γ-C3-MTX was added to each well for 5 minutes with shaking. Beads were resuspended and read in an ECL analyzer. Results are summarized in Table 5.

TABLE 5

The Effect of NADPH in DHFR Assay Buffer on ECL Signal

| TAG γ-$C_3$-MTX (nM) | NADPH (μM) | | |
|---|---|---|---|
| | 0.00 | 1.0 | 5.0 |
| Buffer | 169 | 169 | 168 |
| 0.31 | 4,269 | 25,577 | 29,395 |
| 0.63 | 6,426 | 40,420 | 49,085 |
| 1.25 | 11,328 | 65,882 | 77,703 |
| 2.50 | 15,491 | 92,888 | 113,341 |
| 5.00 | 19,809 | 116,748 | 134,138 |
| 10.0 | 21,480 | 119,484 | 140,688 |
| 20.0 | 21,218 | 118,503 | 143,341 |

TAG γ-C3-MTX at concentrations from 0.31 to 20 nM in the presence of 1.0 μM and 5.0 μM NADPH resulted in higher ECL signals than in the absence of NADPH. These results demonstrated that the NADPH was required to efficiently form DHFR and MTX binding complex.

Example 13—Quantitative Methotrexate Assay Method Using DHFR

Figure 5:
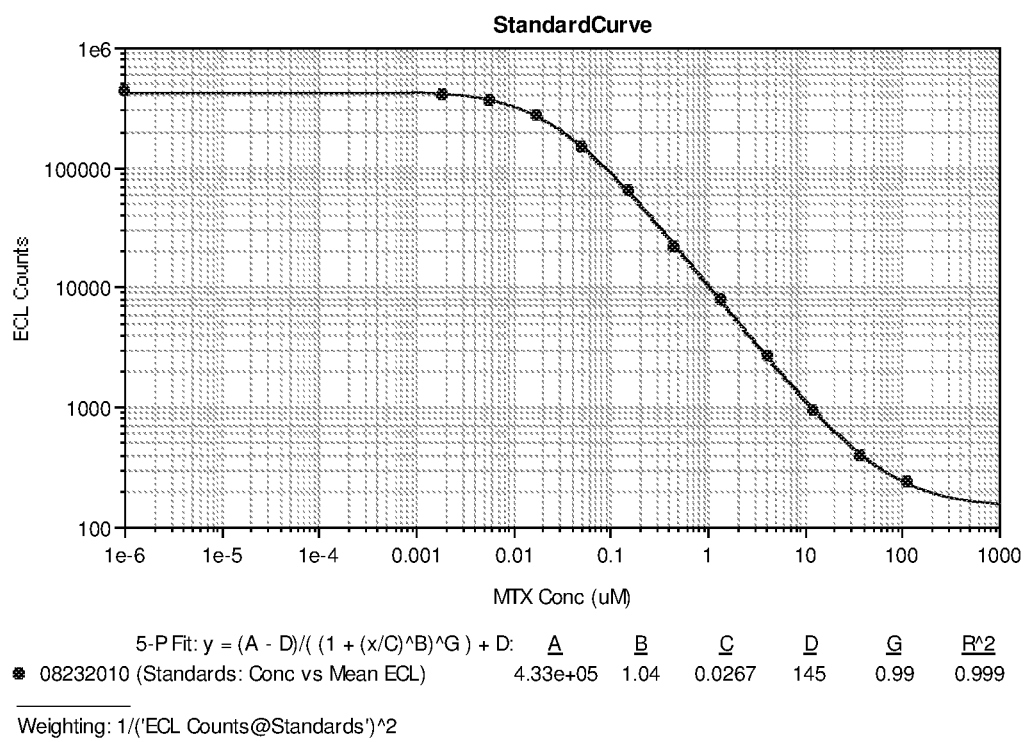
FIG. 5 is a curve showing the dynamic range of an assay of the present disclosure.

TAG γ-C3-MTX was mixed with human plasma containing unlabeled MTX. Capture reagent was then added. Increasing amounts of unlabeled MTX in the human plasma competed with TAG-labeled MTX for binding to DHFR. The ECL signal was inversely proportional to the amount of unlabeled MTX bound to the DHFR. Data from a standard curve is shown in Table 6 and FIG. 5. The results demonstrated that the dynamic range of the assay was from 0.0019 to 111 μM/L.

TABLE 6

Assay Calibrator Curve for Detection of MTX in Human Plasma

| MTX Conc. (μM) | Mean ECL | ECL CV % | Mean Conc. | Conc. CV % | % AR |
|---|---|---|---|---|---|
| CAL01 (0.0) | 429684 | 0.1 | NA | NA | NA |
| CAL02 (0.0019) | 404116 | 1.4 | 0.0021 | 20 | 113 |
| CAL03 (0.0057) | 367880 | 2.2 | 0.0051 | 14 | 90 |
| CAL04 (0.0169) | 272731 | 0.9 | 0.0162 | 2.3 | 96 |
| CAL05 (0.0508) | 145439 | 7.7 | 0.0528 | 11 | 104 |
| CAL06 (0.152) | 63151 | 3.8 | 0.1512 | 4.3 | 100 |
| CAL07 (0.457) | 21897 | 10 | 0.4741 | 11 | 104 |
| CAL08 (1.37) | 7998 | 3.6 | 1.316 | 3.7 | 96 |
| CAL09 (4.12) | 2688 | 7.2 | 4.01 | 7.5 | 97 |
| CAL10 (12.3) | 938 | 2.1 | 12.5 | 2.5 | 102 |
| CAL11 (37) | 392 | 2.0 | 39 | 3.0 | 106 |
| CAL12 (111) | 235 | 0.2 | 105 | 0.4 | 94 |

% AR—Percent Analytical Recovery

It is to be understood that, as used herein, the terms "the," "a," or "an," mean "at least one," and should not be limited to "only one" unless explicitly indicated to the contrary. Unless otherwise indicated, all numbers used in the specification and claims are to be understood as being modified in all instances by the term "about," whether or not so stated. It should also be understood that the precise numerical values used in the specification and claims form additional embodiments of the invention, and are intended to include any ranges which can be narrowed to any two end points within the example ranges and values provided. Efforts have been made to ensure the accuracy of the numerical values disclosed herein. Any measured numerical value, however, can inherently contain certain errors resulting from the standard deviation found in its respective measuring technique.

All publications, patents and patent applications mentioned in this specification are herein incorporated by reference in their entirety into the specification to the same extent as if each individual publication, patent or patent application was specifically and individually indicated to be incorporated herein by reference. Also incorporated by reference is any supplemental information that was published along with any of the aforementioned publications, patents and patent applications. For example, some journal articles are published with supplemental information that is typically available online.

What is claimed is:

1. An isolated antibody that binds to methotrexate (MTX), the antibody comprising a variable heavy chain and a variable light chain, wherein the variable heavy chain nucleotide sequence comprises SEQ ID NO:1 and wherein the variable light chain nucleotide sequence comprises SEQ ID NO:2.

2. An isolated antibody that binds to methotrexate (MTX), the antibody comprising a variable heavy chain and a variable light chain, wherein the variable heavy chain nucleotide sequence comprises SEQ ID NO:5 and wherein the variable light chain nucleotide sequence comprises SEQ ID NO:6.

3. An isolated antibody that binds to methotrexate (MTX), the antibody comprising a variable heavy chain and a variable light chain, wherein the variable heavy chain nucleotide sequence comprises SEQ ID NO:9 and wherein the variable light chain nucleotide sequence comprises SEQ ID NO:10.

4. An isolated antibody that binds to methotrexate (MTX), the antibody comprising a variable heavy chain and a variable light chain, wherein the variable heavy chain amino acid sequence comprises SEQ ID NO:3 and wherein the variable light chain amino acid sequence comprises SEQ ID NO:4.

5. An isolated antibody that binds to methotrexate (MTX), the antibody comprising a variable heavy chain and a variable light chain, wherein the variable heavy chain amino acid sequence comprises SEQ ID NO:7 and wherein the variable light chain amino acid sequence comprises SEQ ID NO:8.

6. An isolated antibody that binds to methotrexate (MTX), the antibody comprising a variable heavy chain and a variable light chain, wherein the variable heavy chain amino acid sequence comprises SEQ ID NO:11 and wherein the variable light chain amino acid sequence comprises SEQ ID NO:12.

7. The method of detecting methotrexate (MTX) in a sample, comprising:

combining in a solution the sample with a capture molecule and a labeled MTX, wherein the capture molecule comprises a solid support and an isolated antibody that binds to methotrexate (MTX), the isolated antibody selected from the group consisting of (1) an antibody comprising a variable heavy chain and a variable light chain, wherein the variable heavy chain nucleotide sequence comprises SEQ ID NO:1 and wherein the variable light chain nucleotide sequence comprises SEQ ID NO:2, (2) an antibody comprising a variable heavy chain and a variable light chain, wherein the variable heavy chain nucleotide sequence comprises SEQ ID NO:5 and wherein the variable light chain nucleotide sequence comprises SEQ ID NO:6, (3) an antibody comprising a variable heavy chain and a variable light chain, wherein the variable heavy chain nucleotide sequence comprises SEQ ID NO:9 and wherein the variable light chain nucleotide sequence comprises SEQ ID NO:10, (4) an antibody comprising a variable heavy chain and a variable light chain, wherein the variable heavy chain amino acid sequence comprises SEQ ID NO:3 and wherein the variable light chain amino acid sequence comprises SEQ ID NO:4, (5) an antibody comprising a variable heavy chain and a variable light chain, wherein the variable heavy chain amino acid sequence comprises SEQ ID NO:7 and wherein the variable light chain amino acid sequence comprises SEQ ID NO:8, or (6) an antibody comprising a variable heavy chain and a variable light chain, wherein the variable heavy chain amino acid sequence comprises SEQ ID NO:11 and wherein the variable light chain amino acid sequence comprises SEQ ID NO:12, wherein the capture molecule is capable of binding the labeled MTX and has less than 6% cross-reactivity with DAMPA (4-Amino-4-deoxy-N-10-methylpteroic acid) in a competitive assay, and wherein MTX when present in the sample competes with the labeled MTX for binding to the capture molecule; and detecting an amount of labeled MTX bound to the capture molecule through a signal produced by the labeled MTX, wherein the signal is inversely proportional to the amount of MTX present in the sample.

8. The method of claim 7, wherein the antibody has less than 1% cross-reactivity with DAMPA (4-Amino-4-deoxy-N-10-methylpteroic acid) in a competitive assay.

9. The method of claim 7, wherein the antibody has less than 1% cross-reactivity with 7-hydroxy-methotrexate (7-OH-MTX) in a competitive assay.

10. The method of claim 7, wherein the antibody has less than 1% cross-reactivity with folic acid in a competitive assay.

11. The method of claim 7, wherein the antibody has less than 1% cross-reactivity with folinic acid in a competitive assay.

12. The method of claim 7, wherein the antibody has less than 2% cross-reactivity with one or more compounds selected from the group consisting of DAMPA (4-Amino- 4-deoxy-N-10-methylpteroic acid), 7-hydroxy-methotrexate (7-OH-MTX), folic acid and folinic acid.

* * * * *